United States Patent [19]

Brugger

[11] Patent Number: 5,591,251
[45] Date of Patent: Jan. 7, 1997

[54] SIDE FLOW BUBBLE TRAP APPARATUS AND METHOD

[75] Inventor: James M. Brugger, Boulder, Colo.

[73] Assignee: COBE Laboratories, Inc., Arvada, Colo.

[21] Appl. No.: 362,262

[22] Filed: Dec. 22, 1994

Related U.S. Application Data

[63] Continuation-in-part of Ser. No. 305,749, Sep. 14, 1994, abandoned, which is a continuation of Ser. No. 158,928, Nov. 19, 1993, abandoned.

[51] Int. Cl.$^6$ .............................. B01D 9/00; A61M 1/14; A61M 3/00
[52] U.S. Cl. ................. 95/242; 95/268; 422/44; 604/4; 604/122; 604/408
[58] Field of Search ........................ 422/44, 47; 604/4, 604/408, 122; 128/DIG. 3; 96/176, 179, 180; 210/436, 645; 95/242, 268

[56] References Cited

U.S. PATENT DOCUMENTS

| | | | |
|---|---|---|---|
| 2,123,809 | 7/1938 | Seitz | 137/592 |
| 2,186,987 | 1/1940 | Nesset | 210/164 |
| 2,528,737 | 11/1950 | Butler | 128/214 |
| 2,586,513 | 2/1952 | Butler | 210/94 |
| 2,675,000 | 4/1954 | Ford | 604/252 |
| 2,693,189 | 11/1954 | Ryan | 604/408 |
| 2,696,818 | 12/1954 | Loghem | 604/252 |
| 2,729,212 | 1/1956 | Butler | 128/214 |
| 2,864,406 | 12/1958 | Schewel | 239/505 |
| 3,045,872 | 7/1962 | Hronas et al. | 222/146.2 |
| 3,221,996 | 12/1965 | Emmert et al. | 239/542 |
| 3,332,418 | 7/1967 | Brody | 91/168 |
| 3,340,871 | 9/1967 | Jellies | 604/251 |
| 3,744,492 | 7/1973 | Leibinsohn | 84/170 |
| 3,778,973 | 12/1973 | Martinez | 96/155 |

(List continued on next page.)

FOREIGN PATENT DOCUMENTS

| | | |
|---|---|---|
| 0058325B1 | 3/1982 | European Pat. Off. . |
| 146708A2 | 7/1985 | European Pat. Off. . |

(List continued on next page.)

OTHER PUBLICATIONS

"Centrysystem® 2 Blood Tubing Sets" brochure, © COBE Laboratories, Inc. 1991, CGH Medical, Inc.,Lakewood, Colorado .

"Drip Chamber, AFM, Blow Molded–Part No. 402351–000", COBE Laboratories, Inc., Lakewood, Colorado.

*Primary Examiner*—Nina Bhat
*Attorney, Agent, or Firm*—Carol W. Burton; Holland & Hart LLP

[57] ABSTRACT

An apparatus for trapping bubbles in blood flowing in a circuit, such as an extracorporeal circuit, includes a housing which defines a substantially vertical chamber having an upper subchamber and a lower subchamber. Blood flowing in a substantially downward direction is introduced into the upper subchamber chamber through a delivery port in a direction substantially transverse to a longitudinal axis of the upper subchamber. A substantially frustoconical deflector is positioned in the chamber opposite and spaced apart from the delivery port. The deflector deflects at least a portion of the blood into the upper subchamber above the deflector. Thereafter, the blood is removed from the chamber out an exit port of the chamber. The deflection and redirection of blood within the chamber provide an opportunity for gases in the blood to separate from the blood in the chamber and also helps prevent stagnation of blood in the chamber which might lead to clotting of the blood. A method of removing bubbles from blood flowing in a circuit involves introducing blood into a substantially vertical chamber at an angle substantially transverse to a longitudinal vertical axis of the chamber. At least a portion of the blood is deflected upward in the chamber by contact with a frustoconical deflector to allow gases to separate from the blood. The blood is then removed from the chamber.

17 Claims, 7 Drawing Sheets

U.S. PATENT DOCUMENTS

| | | | |
|---|---|---|---|
| 3,834,386 | 9/1974 | Sisley | 128/214 |
| 3,965,895 | 6/1976 | Dabney | 604/127 |
| 3,993,066 | 11/1976 | Virag | 604/52 |
| 4,013,072 | 3/1977 | Jess | 604/252 |
| 4,061,031 | 12/1977 | Grimsrud | 73/200 |
| 4,102,655 | 7/1978 | Jeffrey et al. | 96/204 |
| 4,344,777 | 8/1982 | Siposs | 356/349 |
| 4,368,118 | 1/1983 | Siposs | 210/136 |
| 4,395,260 | 7/1983 | Todd et al. | 604/122 |
| 4,493,705 | 1/1985 | Gordon | 604/122 |
| 4,547,190 | 10/1985 | Leason | 604/185 |
| 4,601,712 | 7/1986 | Cole et al. | 604/251 |
| 4,622,032 | 11/1986 | Katsura | 604/122 |
| 4,643,713 | 2/1987 | Viitala | 604/4 |
| 4,666,598 | 5/1987 | Heath et al. | 210/239 |
| 4,681,606 | 7/1987 | Swan, Jr. et al. | 96/197 |
| 4,734,269 | 3/1988 | Clarke | 96/156 |
| 4,806,135 | 2/1989 | Siposs | 96/212 |
| 4,863,452 | 9/1989 | Irmiter | 604/408 |
| 4,900,308 | 2/1990 | Verkaart | 604/126 |
| 4,964,984 | 10/1990 | Reeder et al. | 210/188 |
| 5,061,236 | 10/1991 | Sutherland | 604/4 |
| 5,102,400 | 4/1992 | Leibinsohn | 604/251 |
| 5,120,302 | 6/1992 | Vescovini | 604/4 |
| 5,328,461 | 7/1994 | Utterberg | 604/80 |
| 5,330,425 | 7/1994 | Uttergerg | 604/83 |

FOREIGN PATENT DOCUMENTS

| | | |
|---|---|---|
| 1171047 | 1/1960 | France . |
| 3202582A1 | 9/1982 | Germany . |
| 3720844A1 | 1/1989 | Germany . |
| 57-176370A | 10/1982 | Japan . |
| 854398 | 8/1981 | U.S.S.R. . |

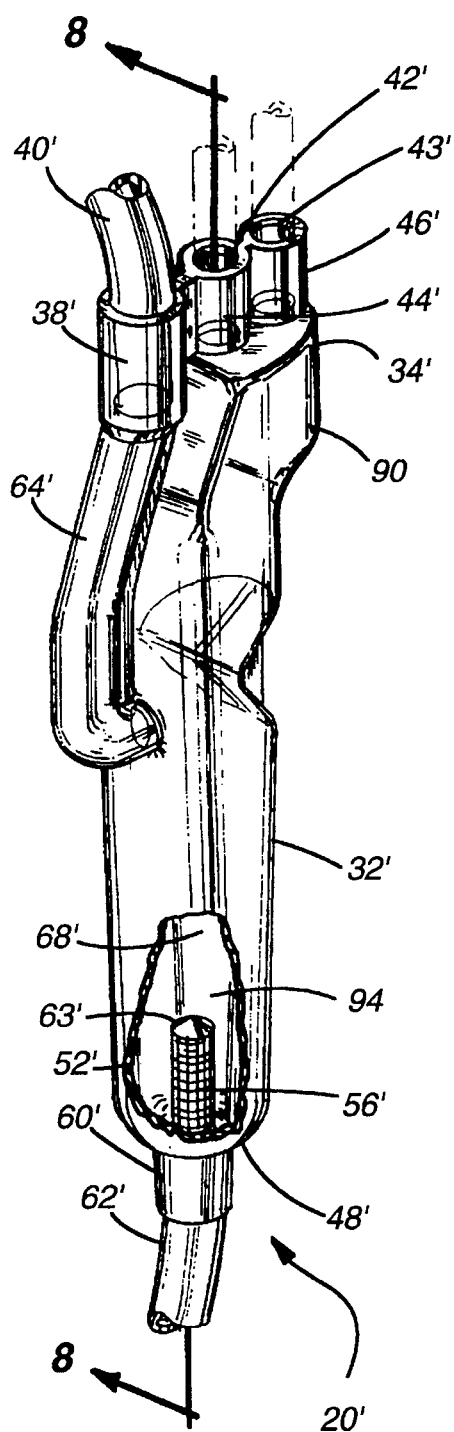
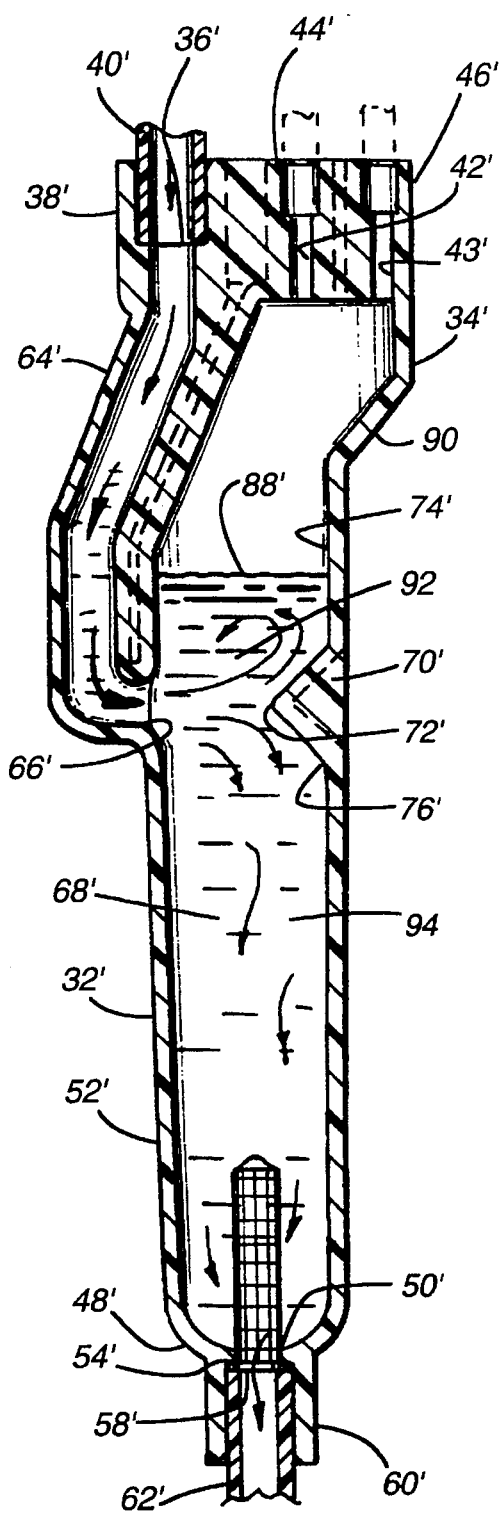
Fig. 7
Fig. 8

SIDE FLOW BUBBLE TRAP APPARATUS AND METHOD

CROSS REFERENCE TO RELATED APPLICATIONS

This application is a continuation-in-part of U.S. patent application Ser. No. 08/305,749, filed Sep. 14, 1994, a File Wrapper Continuation application of U.S. patent application Ser. No. 08/158,928, filed Nov. 29, 1993, all abandoned assigned to the Assignee hereof and now abandoned, and is related to an invention for Top Flow Bubble Trap Apparatus and Method, Ser. No. 08/158,930 filed Nov. 29, 1993, now allowed U.S. Pat. No. 5,503,801 therewith, which is also assigned to the Assignee hereof, the disclosure of which is incorporated herein by reference.

FIELD OF THE INVENTION

This invention relates to bubble trap apparatus and method for the extracorporeal treatment of blood. More particularly this invention relates to new and improved bubble trap apparatus and method that aid in the removal of bubbles from blood and in the prevention of the formation of bubbles in the blood during its extracorporeal treatment.

BACKGROUND OF THE INVENTION

Extracorporeal blood treatment involves removing blood from a patient, treating the blood external to the patient and returning the treated blood to the patient. Occasionally, bubbles form in the blood during extracorporeal blood treatment as a result of leakage of air into the blood at the point blood is withdrawn from the patient for extracorporeal treatment and as a result of leakage of air at points of connection in the extracorporeal treatment system. Bubbles also form as a result of turbulence of the blood flowing in the extracorporeal treatment system and coalescence of gases in the blood during treatment, among other causes. Care must be taken to remove bubbles from the blood prior to returning the blood to the patient and, to the extent possible, prevent formation of bubbles in the blood during treatment. Blood returned to the patient which contains bubbles creates a risk of serious health consequences to the patient.

Sometimes bubbles in blood flowing through extracorporeal treatment systems are optically or sonically detectable and many such systems incorporate equipment capable of detecting these bubbles. When bubbles are detected, the flow of blood returning to the patient is usually halted to prevent return of the detected bubbles to the patient. However, it is preferable that such bubbles be collected and removed from the blood so that blood treatment can continue uninterrupted.

Most extracorporeal treatment systems incorporate chambers for removal of bubbles from blood undergoing treatment. These chambers, often referred to as bubble traps, provide an opportunity for bubbles in the blood to separate from the blood while the blood is in the chamber. Bubbles in the blood rise to the surface of the blood in the chamber. Bubbles in the blood may also separate from the blood as the blood is delivered to the chamber, when the blood is delivered dropwise or in a stream over the surface of the blood already present in the chamber. The gas from the bubbles which collects above the level of blood is mechanically removed from the chamber, or is allowed to remain in the chamber until extracorporeal treatment is complete.

It is possible, however, that smaller bubbles may be present in the blood which may not be collected in the bubble traps of some extracorporeal treatment systems. The patient may then be subject to a risk of injury when these smaller bubbles coalesce into a larger bubble upon aggregation of the bubbles within the patient or may be subject to other risks.

Conditions under which bubbles form in the blood during extracorporeal treatment may be exacerbated by higher blood flow rates. For example, blood entering a bubble trap apparatus at a high rate may froth and create bubbles in the blood present in the bubble trap apparatus. These bubbles could pass through the bubble trap apparatus and remain in the blood to be returned to the patient.

Poor flow patterns can also create problems for blood flowing through a bubble trap apparatus. For example, if blood flow in a bubble trap apparatus is excessively turbulent, the blood's clotting processes may be activated undesireably and blood clots may form in the blood. Also by way of example, incomplete mixing of blood can cause blood in portions of the bubble trap apparatus to stagnate. The stagnated blood is then susceptible to clotting. Clotting of blood in a bubble trap apparatus may result in occlusion of lines of the extracorporeal blood treatment system or injury to the patient.

When blood is introduced into a bubble trap apparatus below the upper surface of the blood already present in the apparatus, stagnation and clotting have a tendency to occur in the blood near the upper surface of the blood. Stagnation and clotting occur near the upper surface of blood because the newly introduced blood tends to flow downward and often does not mix with blood above the point of introduction and near the upper surface. Although these clots may be filtered out of the blood before the blood is returned to the patient, excessive clot formation can occlude filters, which can lead to decreased blood flow to the patient.

One way that clot formation has been minimized is by introducing additional heparin into the blood of the patient. However, excess heparin in a patient can lead to other health problems and therefore excessive use of heparin is not preferred.

It is against this background that the significant improvements and advancements of the present invention have taken place.

SUMMARY OF THE INVENTION

One important aspect of the present invention relates to a bubble trap apparatus in which large and small bubbles are more expeditiously removed from blood while the blood is being treated extracorporeally. Another important aspect of the present invention relates to the minimization of bubble formation during such treatment. Still another aspect is the maintenance of blood flow throughout the apparatus to prevent stagnant areas from forming and thereby help prevent the formation of blood clots.

In accordance with these and other aspects, the present invention relates to an apparatus for trapping bubbles in blood flowing in a circuit, for example an extracorporeal blood treatment circuit, which comprises a housing defining a substantially vertical, longitudinal chamber. Blood is introduced into the chamber through a delivery port in a direction transverse to a longitudinal axis of the chamber. A deflector is positioned within the chamber to deflect at least a portion of the blood introduced into the chamber into a portion of the chamber above the deflector. After deflection, the blood flows generally downward along the length of the chamber and out an exit port of the apparatus. The deflection within the chamber and the flow of blood through the chamber provide an opportunity for bubbles in the blood to separate from the blood while the blood is in the chamber and help prevent stagnation and clotting of blood in the chamber.

In accordance with other aspects, the present invention relates to a method for removing bubbles from blood flowing through an apparatus. Blood is introduced into a substantially vertical chamber of the apparatus in a direction substantially transverse to the vertical axis of the chamber. At least a portion of the blood is deflected into the chamber above the level at which the blood was introduced in the chamber, to provide an opportunity for bubbles in the blood to separate from the blood and help prevent stagnation and clotting of blood in the chamber. Thereafter, the blood is removed from the chamber. An upper surface of the blood is maintained in the chamber above the level at which the blood is introduced to the chamber. Bubbles separating from the blood are collected above the upper surface of the blood.

These and other features of the present invention can be better understood from the following detailed description of a preferred embodiment of the present invention, taken in conjunction with the accompanying drawings that are briefly described below.

BRIEF DESCRIPTION OF THE DRAWINGS

FIG. 7 is a perspective view of another embodiment of the bubble trap apparatus which is an alternative to that shown in FIG. 2.

FIG. 8 is a section view of the bubble trap apparatus taken along the line 8—8 in FIG. 7.

DETAILED DESCRIPTION

Four presently preferred embodiments of apparatus 20, 20', 20" and 20'" for collecting bubbles in blood undergoing extracorporeal treatment are shown in FIGS. 2 through 14. One bubble trap apparatus 20, 20', 20" or 20'" is typically used as a component of an otherwise conventional extracorporeal treatment system 24, shown in FIG. 1.

Figure 1:
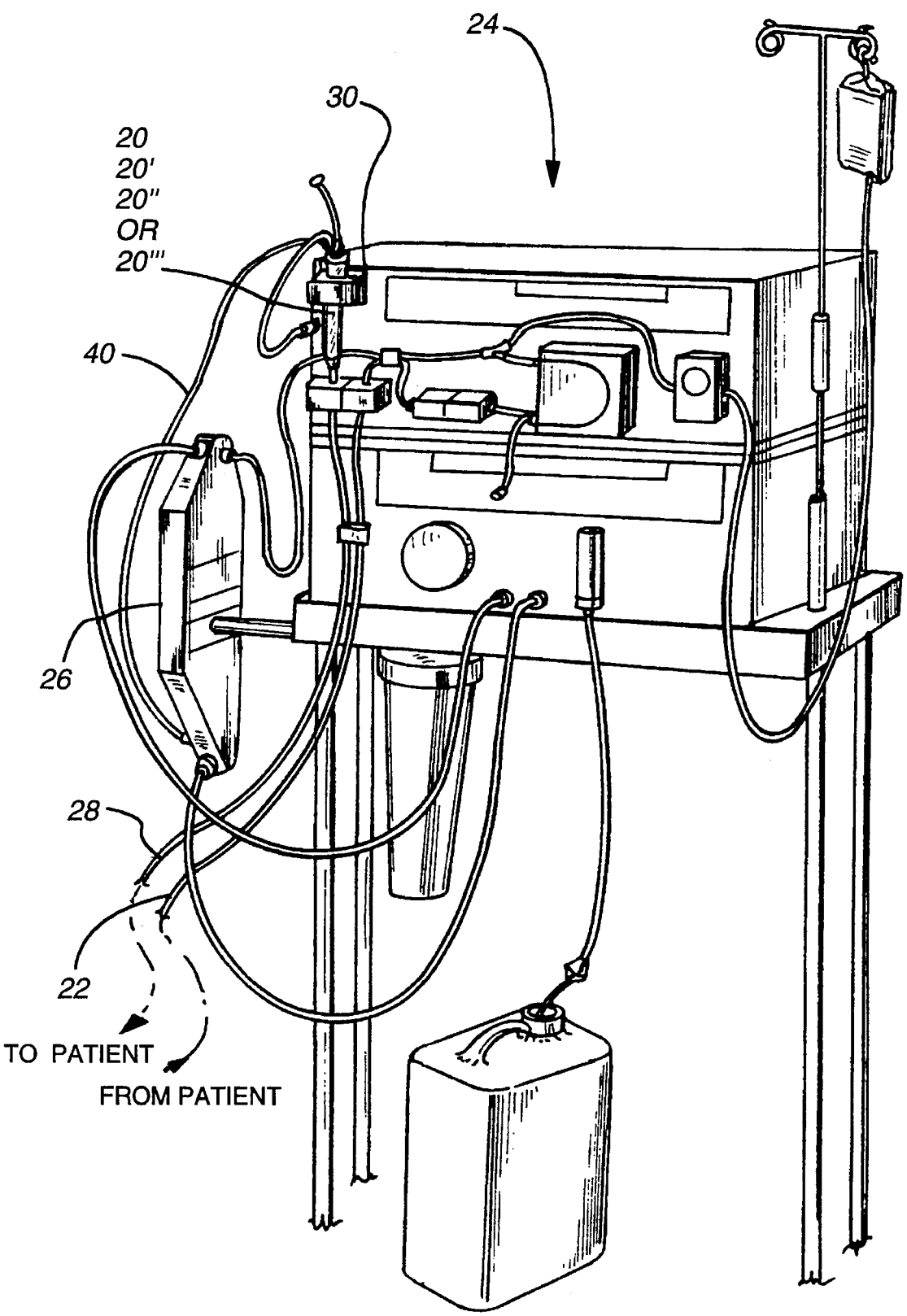
FIG. 1 is a perspective view of an extracorporeal blood treatment system to which a patient undergoing blood treatment is connected, utilizing a bubble trap apparatus incorporating the present invention.

Referring to FIG. 1, blood from a patient is circulated through conduit 22 to an extracorporeal treatment system 24 having a filtration unit 26 through which the blood flows. After passing through the filtration unit 26 the blood passes through the bubble trap apparatus 20, 20', 20" or 20'" attached to the extracorporeal treatment system 24, after which the blood is returned to the patient via conduit 28. A blood level detector 30 of the extracorporeal treatment system 24 is operatively positioned relative to the apparatus 20, 20', 20" or 20'" for detecting changes in the level of blood while the blood is in the apparatus 20, 20', 20" or 20'".

Figure 2:
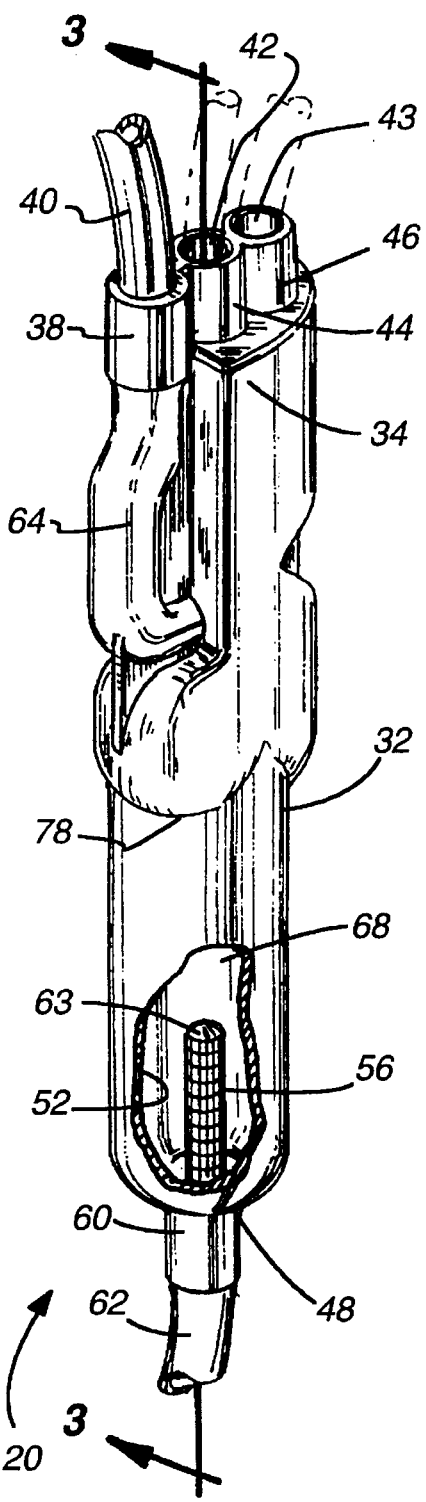
FIG. 2 is a perspective view of the bubble trap apparatus shown in FIG. 1.
Figure 3:
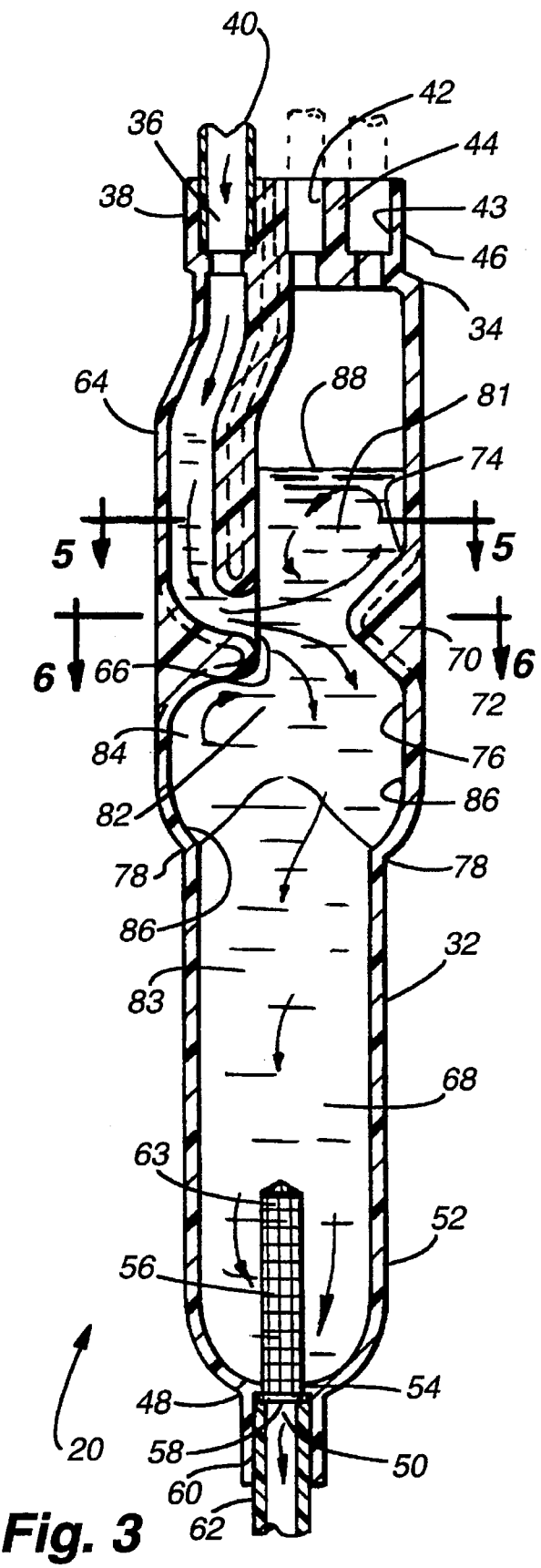
FIG. 3 is a section view of the bubble trap apparatus taken substantially along the section line 3—3 of FIG. 2.
Figure 4:
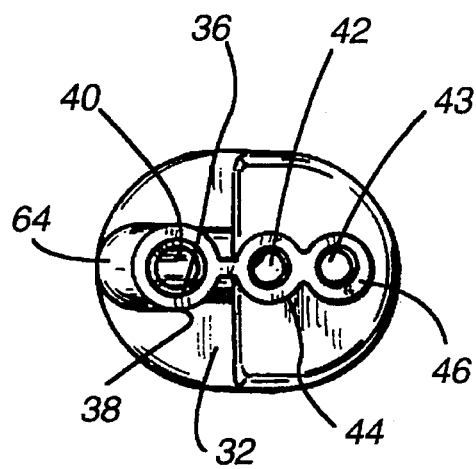
FIG. 4 is a top view of the bubble trap apparatus shown in FIG. 3.

Referring to FIGS. 2 and 3, the bubble trap apparatus 20 includes a substantially elongated hollow housing 32. During use, the housing 32 is aligned vertically along a longitudinal reference or axis of the housing 32, and reference herein to the components of the housing 32 is in relation to the relative orientation of the components during such use as shown in FIGS. 2 and 3. An inlet port 36 is formed in the upper end 34 of the housing 32. Blood is introduced to the apparatus 20 through the inlet port 36. As is shown in FIGS. 2–4, an inlet coupling 38 is also formed in the upper end 34 of the housing 32 and surrounds the inlet port 36. The inlet coupling 38 receivably retains and is solvent bonded to a conduit 40 which is in fluid communication with the extracorporeal treatment system 24 (FIG. 1).

Also formed in the upper end 34 of the housing are first and second apertures 42 and 43. The first aperture 42 is surrounded by a first coupling 44 and the second aperture 43 is surrounded by a second coupling 46. Attached to the second coupling 46 is a device (not shown) for monitoring gas pressure in the bubble trap apparatus 20. The first aperture 42 is typically used for introduction of medication or saline into blood flowing through the bubble trap apparatus 20.

An exit port 50 is formed in the lower end 48 of the housing 32. Blood exits the apparatus 20 through the exit port 50. A collar 54 is formed at the interior junction of the wall 52 of the housing 32 and the exit port 50. A filter 56 with a rim 58 having a diameter greater than the diameter of the collar 54 is inserted through the exit port 50 and is disposed within the apparatus 20, with the rim 58 of the filter 56 positioned below the collar 54. An exit coupling 60 surrounding the exit port 50 receives the rim 58 of the filter 56 and also receivably retains an exit conduit 62. The exit conduit 62 is in fluid communication with a return conduit (not shown). The exit conduit 62 is frictionally engaged by and solvent bonded to the exit coupling 60, with the filter 56 sandwiched between the exit conduit 62 and the collar 54, thereby preventing dislocation of the filter 56 and the exit conduit 62 during extracorporeal treatment. Perforations 63 are formed in the filter 56. The perforations 63 allow blood to pass through the filter 56 and out the exit conduit 62 but are small enough to block particulate matter larger than a predetermined size, such as blood clots and foreign material, from passing into the exit conduit 62 and returning to the patient.

An inlet tube 64 is defined by upper portions of the wall 52 of the housing 32 and extends downward from the inlet port 36. The inlet tube 64 is hollow and extends approximately one third the length of the housing 32 to a point at which it turns perpendicularly towards the center of the housing 32 and becomes transverse to a vertically and longitudinally extending chamber 68 defined by the housing 32. Upon becoming transverse to the longitudinal chamber 68, the inlet tube 64 terminates at a delivery port 66 formed in the inlet tube 64. The delivery port 66 of the inlet tube 64 opens into the chamber 68. The chamber 68 extends upward to the upper end 34 of the housing 32 and downward to the lower end 48 of the housing 32.

Figure 5:
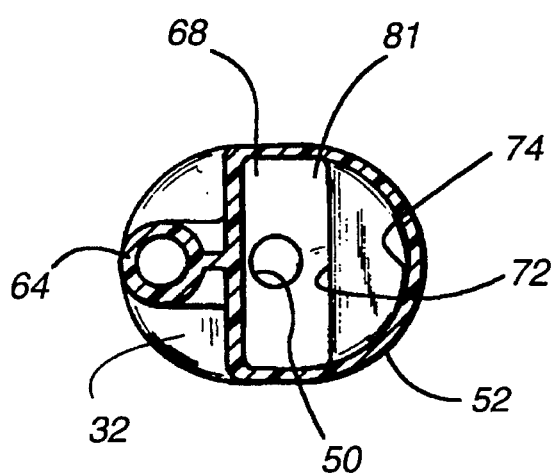
FIG. 5 is a cross-sectional view of the bubble trap apparatus taken substantially along the section line 5—5 in FIG. 3.
Figure 6:
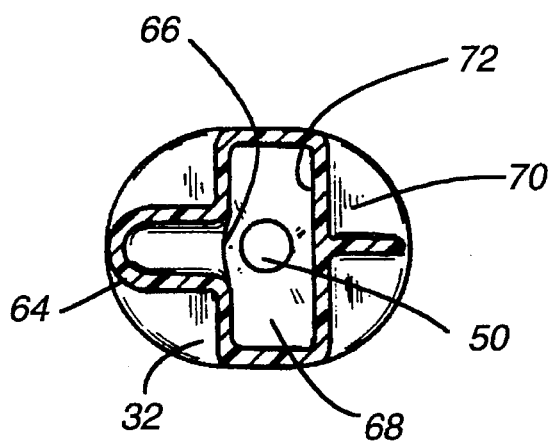
FIG. 6 is a cross-sectional view of the bubble trap apparatus taken substantially along the section line 6—6 in FIG. 3.

Formed in the wall 52 of the housing 32 and opposite the delivery port 66 of the inlet tube 64, is a deflector 70 (FIGS. 3 and 6). The deflector 70 projects inwardly from the housing wall 52 into the chamber 68, effectively narrowing the chamber 68 at the center of the deflector 70 (FIG. 6). The deflector 70 is substantially wedge-shaped with an edge 72 projecting inward toward the chamber 68. The deflector 70 flares outward from the deflector edge 72 to merge into the upper inside surface 74 (FIG. 3, 4 and 5) and lower inside surface 76 (FIG. 3) of the housing wall 52, both of which inside surfaces 74 and 76 are substantially vertical.

The restricted size of the chamber 68 at the deflector edge 72 and a further narrowing of the chamber 68 below the deflector 70 at a neck 78 effectively divide the chamber 68 into first, second and third subchambers 81, 82 and 83, respectively. The first subchamber 81 is generally that portion of the chamber 68 above the deflector edge 72. Due to the flaring of the deflector 70 as it meets the upper inside surface 74 of the housing wall 52, the size of the first subchamber 81 is narrower near the deflector edge 72 and is wider towards the upper end 34 of the housing 32 (FIG. 5). The second subchamber 82 is generally that portion of the chamber 68 below the deflector edge 72 but above the neck 78 of the housing 32. Due to the flaring of the deflector 70 away from the deflector edge 72 as the deflector 70 merges into the lower inside surface 76 of the housing wall 52, and also due to the housing wall 52 extending downward and outward from the delivery port 66 of the inlet tube 64, the second subchamber 82 has a relatively wide midsection 84. The size of the second subchamber 82 narrows at the neck 78. The third subchamber 83 is defined at its upper extreme by the neck 78 and at its lower extreme by the lower end 48 of the housing 32. The third subchamber 83 is generally cylindrical with a substantially constant diameter, except near the lower end 48 of the housing 32 where the housing wall 52 curves gradually and smoothly inwardly to define the exit port 50.

As is shown in FIG. 3, blood flowing in the conduit 40 during extracorporeal treatment first flows through the inlet port 36 and thence downward along the inlet tube 64. The blood is then introduced into the chamber 68 at the delivery port 66, initially flowing in a substantially horizontal direction. Some of the blood entering the chamber 68 is deflected by the deflector 70 upward into the first subchamber 81 to mix with blood already present in the first subchamber 81. The gradual flare of the deflector 70 above the deflector edge 72 encourages blood to mix throughout the first subchamber 81 by directing blood to flow first along the upper flared surface of the deflector 70, then upward along the inside upper surface 74 of the housing wall 52 until the blood approaches the upper surface level 88 of the blood. Gravity then causes the blood to flow downward through the first subchamber 81, during which time the blood mixes with blood already deflected into the first subchamber 81. Stagnation and clotting of blood is substantially avoided in the first subchamber 81 by the absence of recesses and sharp corners in the first subchamber 81 in which blood might otherwise collect and by the fluid movement induced by the deflector 70.

Some of the blood entering the chamber 68 through the delivery port 66 is directed downward into the second subchamber 82 by gravity and by contact with and deflection off of the lower surface of the deflector 70 below the deflector edge 72. Other blood previously circulating in the first subchamber 81 flows downward into the second subchamber 82.

Blood in the second subchamber 82 is encouraged to mix by the narrowing size of the second subchamber 82 between the delivery port 66 and the deflector 70 and at the neck 78. The inwardly curving inner wall 86 of the housing 32 at the neck 78 directs blood flowing down along the inside housing wall towards the midsection 84 of the second subchamber 82. Some of the blood directed toward the midsection 84 is deflected by other portions of the curving inner wall 86, to mix with blood entering the second subchamber 82 from above. The absence of recesses and sharp corners in the second subchamber 82 substantially prevents stagnation of blood while the blood is undergoing mixing in and passing through the second subchamber 82.

Gases in the blood are given an opportunity to coalesce into bubbles, and these bubbles and bubbles already present in the blood are given an opportunity to float upward to the upper surface 88 of the blood in the first subchamber 81 while blood is in the chamber 68. In addition, bubbles present in the blood are urged upward toward the upper surface 88 of the blood in the chamber 68 by redirection of blood flow upward into the first subchamber 81 and circulation of blood upward within the first and second subchambers 81 and 82. The bubbles collect above the blood level 88 in the chamber 68. The upper surface 88 is preferably maintained in the first subchamber 81 at a level intermediate between the upper end 34 of the housing 32 and the deflector edge 72.

Gravity forces blood in the second subchamber 82 to flow downward into the third subchamber 83. After flowing the length of the third subchamber 83, the blood passes through perforations 63 in the filter 56, out the exit port 50 and into the exit conduit 62.

The neck 78 formed in the wall 52 of the housing 32 also serves to help align the bubble trap apparatus 20 during mounting to an extracorporeal treatment system 24 (FIG. 1). The wider portion of the apparatus 20 above the neck 78 contrasts with the narrower portion of the apparatus 20 below the neck 78 and functions as a stopper or wedge when the apparatus 20 is placed in a receiving clamp (not shown) of the extracorporeal treatment system 24. When functioning as a stopper, the widened portion of the apparatus 20 above the neck 78 prevents the apparatus 20 from incorrect alignment initially and from undesirably sliding downward during the course of the extracorporeal treatment.

An alternate embodiment 20' of an improved bubble trap apparatus is shown in FIGS. 7 and 8. The apparatus 20' includes similar features as those of the apparatus 20 which are referenced by like primed numerals. The apparatus 20' includes a substantially elongated hollow housing 32', albeit slightly bent at its upper end 34', During use, the apparatus 20' is aligned vertically along a longitudinal reference or axis of the housing 32', and reference herein to the components of the housing 32' is in relation to the relative orientation of the components during such use. An inlet port 36' is formed in the upper end 34' of the housing 32'. Blood is introduced to the apparatus 20' through the inlet port 36'. An inlet coupling 38' is formed in the upper end 34' of the housing 32' and surrounds the inlet port 36'. The inlet coupling 38' receivably retains and is solvent bonded to a conduit 40' which is in fluid communication with an extracorporeal treatment system.

Also formed in the upper end 34' of the housing are first and second apertures 42' and 43'. The first aperture 42' is surrounded by a first coupling 44' and the second aperture 43' is surrounded by a second coupling 46'. A device (not shown) for monitoring gas and pressure in the bubble trap apparatus 20' is attached to the first coupling 44'. The second aperture 43' is typically used for introduction of medication or saline into blood flowing through the bubble trap apparatus 20'. An angled portion 90 of the housing 32' is adjacent to the second aperture 43' so that saline, medication or other material introduced into the chamber 68' through the second aperture 43' flows along the angled portion 90 rather than free falling into the blood in the apparatus and possibly causing undesirable spattering and frothing.

An exit port 50' is formed in the lower end 48' of the housing 32'. Blood exits the apparatus 20' through the exit port 50'. Formed at the interior junction of the wall 52' of the housing 32' and the exit port 50' is a collar 54'. A filter 56' with a rim 58' having a diameter wider than the diameter of the collar 54' is inserted through the exit port 50' and is disposed within the apparatus 20'. The rim 58' of the filter 56' is wider than the collar 54' and the filter 56' is fixedly positioned at the lower end 48' of the housing 32' adjacent to the exit port 50'. An exit coupling 60' surrounds the exit port 50' and receives the rim 58' of the filter 56' and also receivably retains exit conduit 62'. The exit conduit 62' is frictionally engaged by and solvent bonded to the exit coupling 60' with the filter 56' sandwiched between the exit conduit 62' and the collar 54', thereby preventing dislocation of the filter 56' and exit conduit 62' during extracorporeal treatment.

An inlet tube 64' is defined by upper portions of the wall 52' of the housing 32' and extends downward from the inlet port 36'. The inlet tube 64' is hollow and extends approximately one half the length of the housing 32' to a point at which the inlet tube 64' turns perpendicularly towards the center of the vertical longitudinal chamber 68' defined by the housing 32' and becomes transverse thereto. Upon becoming transverse to the longitudinal chamber 68', the inlet tube 64' terminates at a delivery port 66' formed in the inlet tube 64' and opens into the chamber 68'. The chamber 68' extends upward to the upper end 34' of the housing 32' and downward to the lower end 48' of the housing 32'.

A substantially wedge-shaped deflector 70' is formed in the wall 52' of the housing 32' and opposite the delivery port 66' of the inlet tube 64'. The deflector 70' projects inwardly from the housing wall 52' into the chamber 68' and terminates at a deflector edge 72', effectively narrowing the size of the chamber 68' at the edge 72' of the deflector 70'. The deflector 70' flares radially from the deflector edge 72' to merge into the upper inside surface 74' and lower inside surface 76' of the housing wall 52'.

The narrowed size of the chamber 68' at the deflector edge 72' effectively divides the chamber 68' into upper and lower subchambers 92 and 94. The upper subchamber 92 is generally that portion of the chamber 68' above the deflector edge 72'. Due to the flaring of the deflector 70' as it meets the upper inside surface 74' of the housing wall 52', the size of the upper subchamber 92 is narrower at the deflector tip 70' and wider where the deflector 70' meets the upper inside surface 74'. The lower subchamber 94 is generally that portion of the chamber 68' below the deflector edge 72'. The lower subchamber 94 is generally cylindrical with a substantially constant diameter, except at its upper end adjacent to the deflector 70' and near the lower end 48' of the housing 32' where the housing wall 52' curves gradually and smoothly inwardly to define the exit port 50'.

As is shown in FIG. 8, blood flowing through the apparatus 20' first flows through the inlet port 36' and thence downward along the inlet tube 64'. The blood is then introduced into the chamber 68' at the delivery port 66', initially flowing in a substantially horizontal direction. A portion of the blood entering the chamber 68' is deflected by the deflector 70' upward into the upper subchamber 92 to mix with blood already present in the upper subchamber 92. The gradual upward flare of the deflector 70' above the deflector edge 72' directs the blood upwards along the upper inner wall 74'. As the blood nears the upper surface 88' of the blood in the upper subchamber 92 the blood begins to flow downward, mixing with other blood present in the upper subchamber 92. Blood circulating in the upper subchamber 92 eventually flows downward into the lower subchamber 94. Stagnation and clotting of blood is substantially avoided in the upper subchamber 92 by the absence of recesses and sharp corners in the upper subchamber 92 in which blood might otherwise collect and by the fluid movement induced by the deflector 70'.

Some of the blood entering the chamber 68' is directed downward into the lower subchamber 94 by gravity and by contact with and deflection off of the lower surface of the deflector 70' which is below the deflector edge 72'. Gravity forces blood in the lower subchamber 94 to flow downward toward the exit port 50'. After flowing the length of the lower subchamber 94, the blood passes through perforations 63' in the filter 56', out the exit port 50' and into the exit conduit 62'.

Gases in the blood are given an opportunity to coalesce into bubbles, and the bubbles are given an opportunity to float upward to the blood level 88' in the upper subchamber 92 and while the blood flows through the upper and lower subchambers 92 and 94. Bubbles present in the blood flowing through the apparatus 20' are urged upward toward the surface of the blood in the chamber 68' by redirection of blood flow upward into the upper subchamber 92 and circulation of blood upward within the upper subchamber 92. The bubbles collect above the level of blood 88' in the upper subchamber 92, which is preferably maintained in the upper subchamber 92 at a level intermediate between the upper end 34' of the housing 32' and the deflector edge 72'.

The increased size of the upper and lower subchambers 92 and 94 of the chamber 68' as compared to the inside diameter of the inlet tube 64' means that blood flowing through the inlet tube 64' typically slows upon entering the chamber 68'. This decrease in blood flow rate makes it easier for bubbles in the blood to separate from the blood and float upward through chamber 68' to the upper blood surface 88' in the upper subchamber 92.

Figure 9:
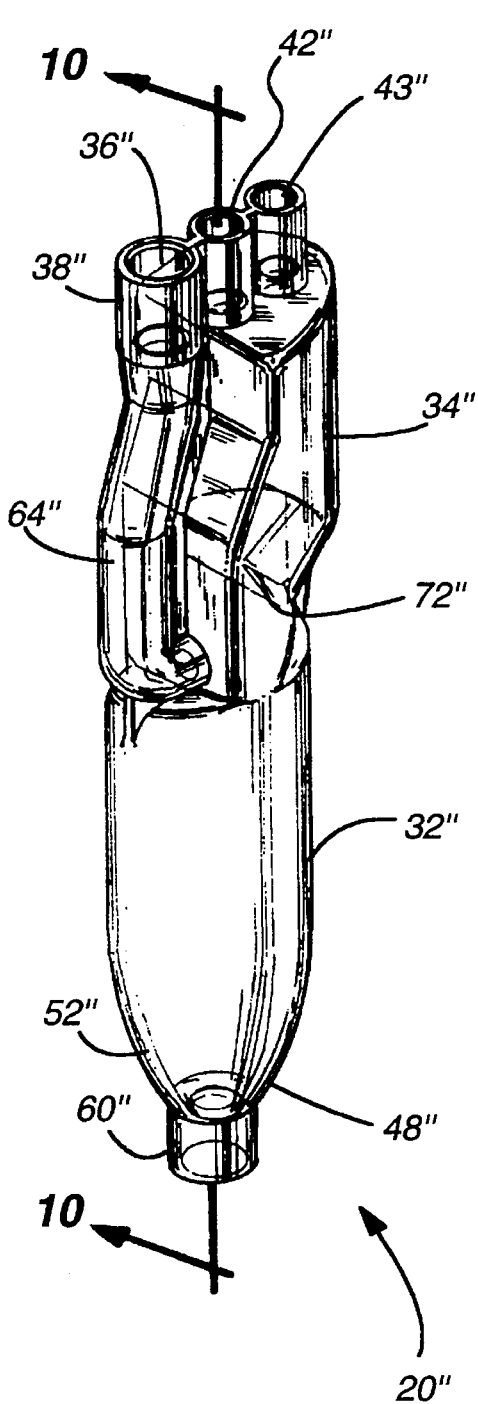
FIG. 9 is a perspective view of another embodiment of the bubble trap apparatus which is an alternative to those shown in FIGS. 2 and 7.
Figure 10:
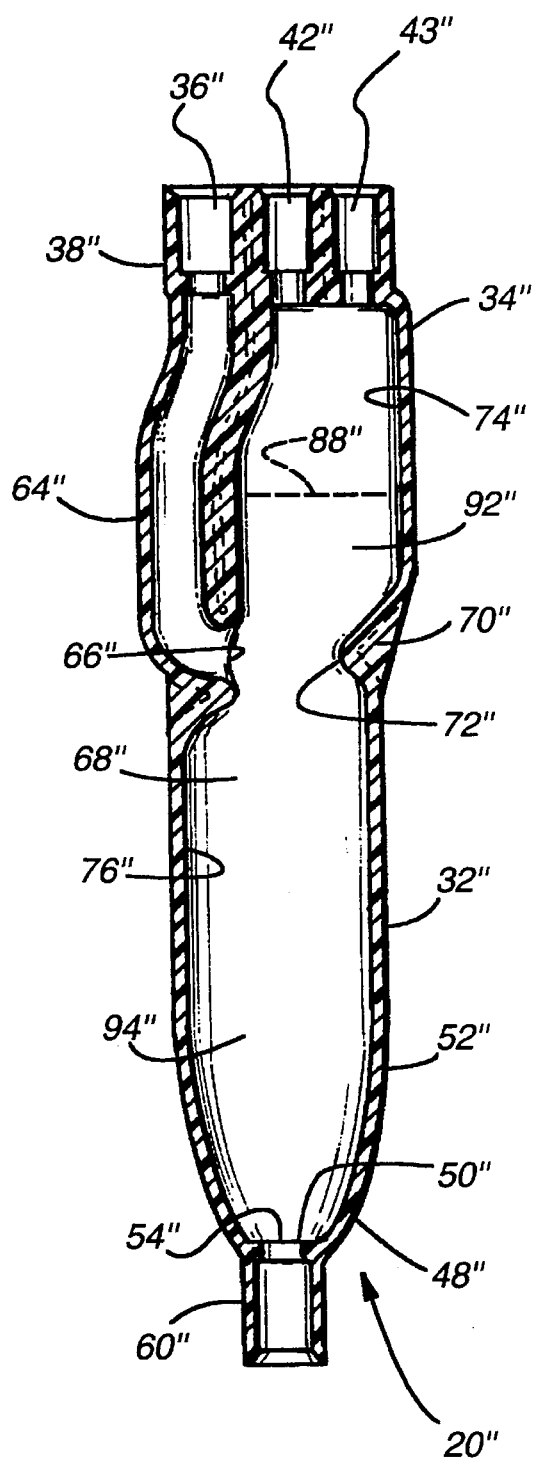
FIG. 10 is a section view of the bubble trap apparatus taken along the line 10—10 in FIG. 9.

An alternate embodiment 20" of an improved bubble trap apparatus is shown in FIGS. 9 and 10. The apparatus 20" includes similar features as those of the apparatus 20 and 20' which are referenced by like double-primed numerals. The apparatus 20" includes a substantially elongated hollow housing 32". During use, the apparatus 20" is aligned vertically along a longitudinal reference or axis of the housing 32", and reference herein to the components of the housing 32" is in relation to the relative orientation of the components during such use. An inlet port 36" is formed in the upper end 34" of the housing 32" through which blood is introduced to the apparatus 20". An inlet coupling 38", which is formed in the upper end 34" of the housing 32", surrounds the inlet port 36" and receivably retains and is solvent bonded to a conduit (not shown) which is in fluid communication with an extracorporeal treatment system. Also formed in the upper end 34" of the housing are first and second apertures 42" and 43", for purposes previously described in connection with apparatus 20.

Referring to FIG. 10, an exit port 50" is formed in the lower end 48" of the housing 32" through which blood exits the apparatus 20". Formed at the interior junction of the wall 52" of the housing 32" and the exit port 50" is a collar 54". Although not shown in FIGS. 9 and 10, as described above in connection with the apparatus 20 and 20', a filter having a rim (not shown) is optionally positioned adjacent to the exit port 56" to prevent blood clots and other materials from passing through the exit port 56" in the blood being returned to the patient. An exit coupling 60" surrounds the exit port 50". Exit conduit (not shown) is frictionally engaged by and solvent bonded to the exit coupling 60" to prevent dislocation of the exit conduit during extracorporeal treatment. If the optional filter is used, the rim of the filter is sandwiched between the exit conduit and the collar 54".

An inlet tube 64" is defined by upper portions of the wall 52" of the housing 32" and extends downward from the inlet port 36". The inlet tube 64" is hollow and extends slightly less than one half the length of the housing 32" to a point at which the inlet tube 64" turns perpendicularly towards the center of the vertical longitudinal chamber 68" defined by the housing 32" and becomes transverse thereto. Upon becoming transverse to the longitudinal chamber 68", the inlet tube 64" terminates at a delivery port 66" formed in the inlet tube 64" and opens into the chamber 68". The chamber 68" extends upward to the upper end 34" of the housing 32" and downward to the lower end 48" of the housing 32".

A substantially wedge-shaped deflector 70" is formed in the wall 52" of the housing 32" and opposite the delivery port 66" of the inlet tube 64". The deflector 70" projects inwardly from the housing wall 52" into the chamber 68" and terminates at a deflector edge 72", effectively narrowing the size of the chamber 68" at the deflector edge 72". The deflector 70" flares upward from the deflector edge 72" to merge into the upper inside surface 74" and flares downward from the deflector edge 72" to merge into the lower inside surface 76" of the housing wall 52".

The narrowed size of the chamber 68" at the deflector edge 72" effectively divides the chamber 68" into upper and lower subchambers 92" and 94". The upper subchamber 92" is generally that portion of the chamber 68" above the deflector edge 72". Due to the flaring of the deflector 70" as it meets the upper inside surface 74' of the housing wall 52", the size of the upper subchamber 92" is narrower at the deflector tip 70" and wider where the deflector 70" meets the upper inside surface 74". The lower subchamber 94" is generally that portion of the chamber 68" below the deflector edge 72". The lower subchamber 94" is generally cylindrical, except at its upper end adjacent to the deflector 70" and towards the lower end 48" of the housing 32" where the housing wall 52" tapers inwardly to define the exit port 50".

As is shown in FIG. 10, blood flowing through the apparatus 20" first flows through the inlet port 36" and thence downward along the inlet tube 64". The blood is then introduced into the chamber 68" at the delivery port 66", initially flowing in a substantially horizontal direction. A portion of the blood entering the chamber 68" is deflected by the deflector 70" upward into the upper subchamber 92" to mix with blood already present in the upper subchamber 92". The gradual upward flare of the deflector 70" above the deflector edge 72" directs the blood upwards along the upper inner wall 74". As the blood nears the upper surface 88" of the blood in the upper subchamber 92" the blood begins to flow downward, mixing with other blood present in the upper subchamber 92". Blood circulating in the upper subchamber 92" eventually flows downward into the lower subchamber 94". Stagnation and clotting of blood is substantially avoided in the upper subchamber 92" by the absence of recesses and sharp corners in the upper subchamber 92" in which blood might otherwise collect and by the fluid movement induced by the deflector 70".

Some of the blood entering the chamber 68" is directed downward into the lower subchamber 94" by gravity and by contact with and deflection off of the lower surface of the deflector 70" which is below the deflector edge 72". Gravity forces blood in the lower subchamber 94" to flow downward toward the exit port 50". After flowing the length of the lower subchamber 94', the blood is directed towards the exit port 50" by the tapered inner wall 52" near the exit port 50", and passes out the exit port 50" and into the exit conduit.

Gases in the blood are given an opportunity to coalesce into bubbles, and the bubbles are given an opportunity to float upward to the upper surface 88" of blood in the upper subchamber 92" and while the blood flows through the upper and lower subchambers 92" and 94". Bubbles present in the blood flowing through the apparatus 20" are urged upward toward the surface 88" of the blood in the chamber 68" by redirection of blood flow upward into the upper subchamber 92" and circulation of blood upward within the upper subchamber 92". The bubbles collect above the upper surface 88" of the blood in the upper subchamber 92", which is preferably maintained in the upper subchamber 92" at a level intermediate between the upper end 34" of the housing 32" and the deflector edge 72".

The increased size of the upper and lower subchambers 92" and 94" as compared to the inside diameter of the inlet tube 64" means that blood flowing through the inlet tube 64" typically slows upon entering the chamber 68". This decreases in blood flow rate makes it easier for bubbles in the blood to separate from the blood and float upward through chamber 68" to the upper surface 88" of the blood in the upper subchamber 92".

Yet another alternate embodiment 20''' of an improved bubble trap apparatus is shown in FIGS. 11–14. The apparatus 20''' includes similar features as those of the apparatus 20, 20' and 20" which are referenced by like thrice-primed numerals. The apparatus 20''' is preferably constructed of substantially transparent, flexible polyvinyl chloride using conventional blow molding techniques. Blow molded polyvinyl chloride plastic is preferred, in part because portions of the walls of the apparatus 20''' meet in substantially curved intersecting regions, thereby avoiding the formation of angular pockets which might otherwise trap blood. However, blow molded polyvinyl chloride is subject to distortion under the elevated temperatures and pressures of extracorporeal treatment. Features of the apparatus 20''' which control the tendency of blow molded polyvinyl chloride to distort are further described below.

Figure 11:
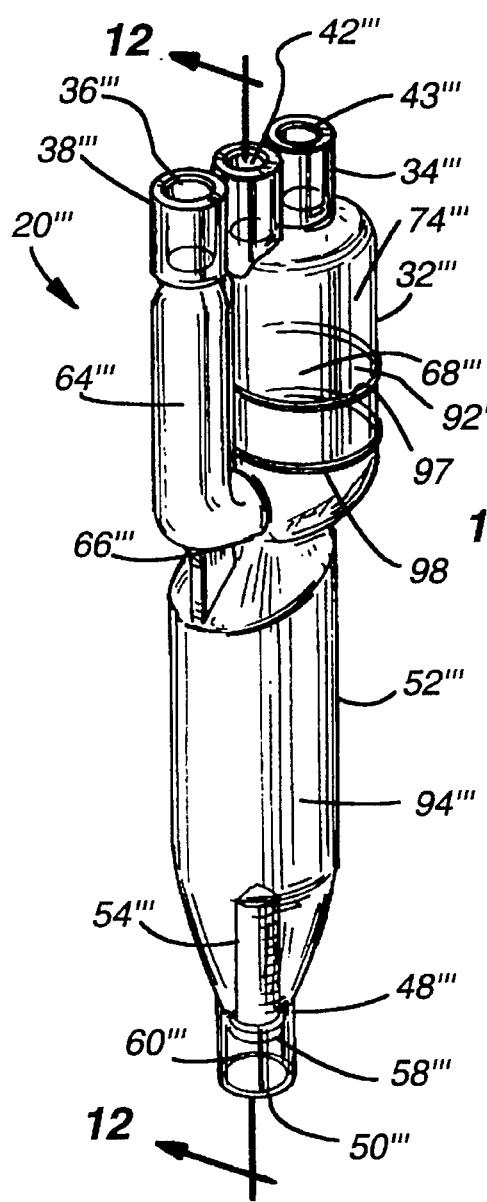
FIG. 11 is a perspective view of another embodiment of the bubble trap apparatus which is an alternative to those shown in FIGS. 2, 7 and 9.
Figure 12:
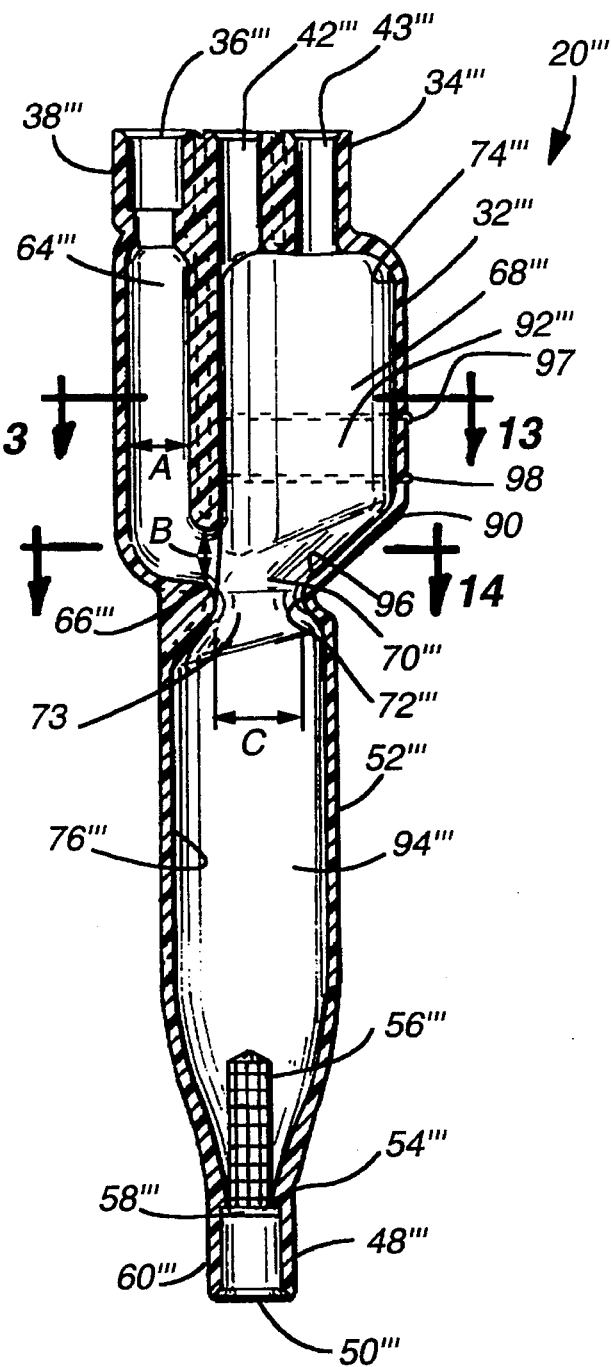
FIG. 12 is a section view of the bubble trap apparatus taken along the line 12—12 in FIG. 11.
Figure 13:
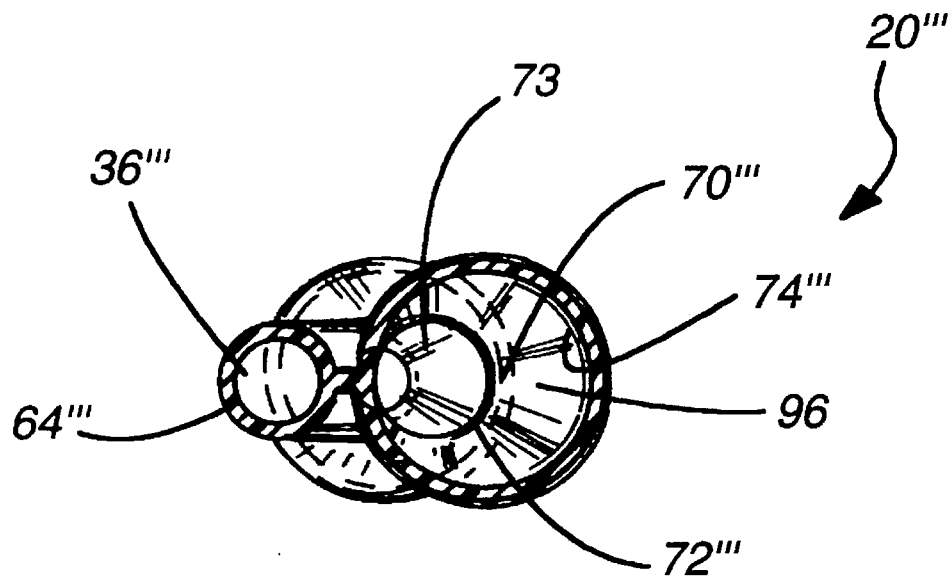
FIG. 13 is a horizontal section view of the bubble trap apparatus taken along the line 13—13 in FIG. 12.
Figure 14:
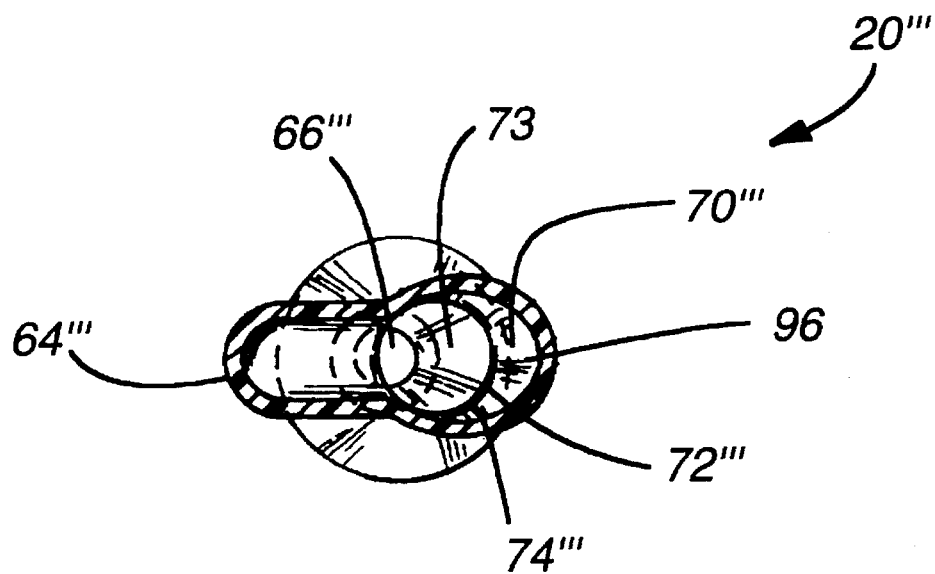
FIG. 14 is horizontal section view of the bubble trap apparatus taken along the line 14—14 in FIG. 12.

Referring now to FIGS. 11 and 12, the apparatus 20''' includes a substantially elongated hollow housing 32'''. During use, the apparatus 20''' is aligned vertically along a longitudinal reference or axis of the housing 32''', and reference herein to the components of the housing 32''' is in relation to the relative orientation of the components during such use. An inlet port 36''' is formed in the upper end 34''' of the housing 32''' through which blood is introduced to the apparatus 20'''. An inlet coupling 38''', which is formed in the upper end 34''' of the housing 32''', surrounds the inlet port 36''' and receivably retains and is solvent bonded to a conduit (not shown) which is in fluid communication with an extracorporeal treatment system. Also formed in the upper end 34''' of the housing are first and second apertures 42''' and 43''', for purposes previously described in connection with apparatus 20 and 20''.

An exit port 50''' is formed in the lower end 48''' of the housing 32''' through which blood exits the apparatus 20'''. Formed at the interior junction of the wall 52''' of the housing 32''' and the exit port 50''' is a collar 54'''. As described above in connection with the apparatus 20, 20' and 20''', a filter 56''' having a rim 58''' is optionally positioned adjacent to the exit port 50''' to prevent blood clots and other materials from passing through the exit port 50''' in the blood being returned to the patient. An exit coupling 60''' surrounds the exit port 50'''. Exit conduit (not shown) is frictionally engaged by and solvent bonded to the exit coupling 60''' to prevent dislocation of the exit conduit during extracorporeal treatment. If the optional filter 56''' is used, the rim 58''' of the filter is sandwiched between the exit conduit and the collar 54'''.

An inlet tube 64''' is defined by upper portions of the wall 52''' of the housing 32''' and extends downward from the inlet port 36'''. The inlet tube 64''' is hollow and extends slightly less than one half the length of the housing 32''' to a point at which the inlet tube 64''' turns perpendicularly towards the center of the vertical longitudinal chamber 68''' defined by the housing 32''' and becomes transverse thereto. Upon becoming transverse to the longitudinal chamber 68''', the inlet tube 64''' terminates at a delivery port 66''' formed in the inlet tube 64''' and opens into the chamber 68'''. The chamber 68''' extends upward to the upper end 34''' of the housing 32''' and downward to the lower end 48''' of the housing 32'''.

A substantially frustoconical deflector 70''' is formed in the wall 52''' of the housing 32''' and opposite the delivery port 66''' of the inlet tube 64'''. The deflector 70''' projects inwardly from the housing wall 52''' into the chamber 68''' and terminates at a deflector edge 72''', effectively narrowing the diameter of the chamber 68''' at the deflector edge 72''' to form a narrow channel 73 of the chamber 68'''. The deflector 70''' flares upward from the deflector edge 72''' to merge into the upper inside surface 74''' at shoulder 95 and flares downward from the deflector edge 72''' to merge into the lower inside surface 76''' of the housing wall 52'''. The deflector face 96, which is that portion of the deflector 70''' between the edge 95 which is arcuate in cross section (FIG. 12) and the deflector edge 70''' is flat in the vertical direction.

The narrow channel 73 of the chamber 68''' at the deflector edge 72''' effectively divides the chamber 68''' into upper and lower subchambers 92''' and 94'''. The upper subchamber 92''', which is substantially cylindrical, is generally that portion of the chamber 68''' above the deflector edge 72'''. Due to the narrowing of the deflector 70''' from the shoulder 95 to the deflector edge 72''', the diameter of the upper subchamber 92''' is narrowest at the deflector tip 70''' (i.e. the channel diameter "C" of FIG. 12) and widest where the edge 95 meets the upper inside surface 74'''.

Upper and lower level indicator marks 97 and 98, respectively, are formed on the outside of the housing wall 52'''. Although in the apparatus 20''' the marks 97 and 98 project outwardly from the wall 52''', they may also be engraved into the wall 52''' or otherwise permanently imprinted on the wall 52'''.

The lower subchamber 94''' is generally that portion of the chamber 68''' below the deflector edge 72'''. The lower subchamber 94''' is generally cylindrical, except at its upper end adjacent to the deflector 70''' and towards the lower end 48''' of the housing 32''' where the housing wall 52''' tapers inwardly to define the exit port 50'''.

Blood flowing through the apparatus 20''' first flows through the inlet port 36''' and thence downward along the inlet tube 64'''. The blood is then introduced into the chamber 68''' at the delivery port 66''', initially flowing in a substantially horizontal direction. A substantial portion of the blood entering the chamber 68''' is deflected by contact with the deflector face 96 upward into the upper subchamber 92''' to mix with blood already present in the upper subchamber 92'''. As the blood nears the upper surface (not shown) of the blood in the upper subchamber 92''' the blood begins to flow downward, mixing with other blood present in the upper subchamber 92'''. Blood circulating in the upper subchamber 92''' eventually flows downward into the lower subchamber 94'''. Stagnation and clotting of blood is substantially avoided in the upper subchamber 92''' by the absence of recesses and sharp corners in the upper subchamber 92''' in which blood might otherwise collect and by the fluid movement induced by the deflector 70'''.

Some of the blood entering the chamber 68''' is directed downward into the lower subchamber 94''' by gravity. Gravity also forces blood in the lower subchamber 94''' to flow downward toward the exit port 50'''. After flowing the length of the lower subchamber 94', the blood is directed towards the exit port 50''' by the tapered inner wall 52''' near the exit port 50''', and passes out the exit port 50''' and into the exit conduit.

Gases in the blood are given an opportunity to coalesce into bubbles, and the bubbles are given an opportunity to float upward to the upper surface 88''' of blood in the upper subchamber 92''' and while the blood flows through the upper and lower subchambers 92''' and 94'''. Bubbles present in the blood flowing through the apparatus 20''' are urged upward toward the surface 88''' of the blood in the chamber 68''' by redirection of blood flow upward into the upper subchamber 92''' and circulation of blood upward within the upper subchamber 92'''. The bubbles collect above the upper surface 88''' of the blood in the upper subchamber 92''', which is preferably maintained in the upper subchamber 92''' at a level intermediate between the upper end 34''' of the housing 32''' and the deflector edge 72''', most preferably between the upper and lower level indicator marks 97 and 98.

The increased size of the upper and lower subchambers 92''' and 94''' as compared to the inside diameter of the inlet tube 64''' means that blood flowing through the inlet tube 64''' typically slows upon entering the chamber 68'''. This decrease in blood flow rate makes it easier for bubbles in the blood to separate from the blood and float upward through chamber 68''' to the upper surface 88''' of the blood in the upper subchamber 92'''.

Certain proportions and shapes of the apparatus 20''' have been found to be important to the performance of the apparatus 20''' as blood passes therethrough. For example, blood flow should not slow as blood travels along the inlet tube 64''', but rather should slow upon entering the upper subchamber 92'''. To avoid premature decrease in blood flow rate within the inlet tube 64''', the diameter "A" of the delivery port 66''' at the plane of intersection with the chamber 68''' should be substantially the same as the diameter "B" of the inlet tube 64''' below the inlet port 36''' (see FIG. 13). A diameter "B" of approximately 5.7 millimeters is most preferred. If the flow of blood entering the chamber 68''' from the inlet tube 64''' is too slow, the blood may be unable to overcome gravitational forces and will flow downward into the lower subchamber 94''' without reaching the deflector 70''', deflecting into the upper subchamber 92''' and degassing therein.

In order to maximize deflection of blood flowing from the inlet tube 64''' into the upper subchamber 92''', the inlet tube 64''' preferably turns perpendicularly towards the upper subchamber 92''' in a relatively sharp angle. A relatively sharp curve, preferably having an internal radius of curvature of from 0.5 to 3.0 millimeters (mm), and most preferably from 1.5 to 2.5 mm, is desired to direct the blood exiting the delivery port across the channel 73 to the deflector face 96.

It is also important that the diameter "C" of the chamber 68''' at the deflector edge 72''' be sufficiently narrow so that the blood exiting the delivery port flow across the channel 73 and reach the deflector face 96. A channel diameter "C" of approximately 11 millimeters is most preferred. If the diameter "C" of the chamber 68''' is excessively large, blood entering the chamber 68''' from the inlet tube 64''' will not have sufficient momentum to contact the face 96 of the deflector 70''' and be deflected thereby into the upper subchamber 92'''. Instead, such blood will flow from the inlet tube 64''' directly downward into the lower subchamber 94''' without deflecting into the upper subchamber 92''' and being degassed therein.

As is clear from the above discussion, the structural relationships of the channel diameter "C" to other features of the apparatus 20''' help the blood maintain sufficient momentum as it flows through the apparatus 20'''. These relationships can be expressed as a product of channel diameter "C" multiplied times the square of inlet port diameter "B" (i.e. $C \times B^2$). Given expected blood flow rates through the apparatus 20''' of from 50 to 700 milliliters per minute, when each of "B" and "C" are measured in millimeters, the preferred product is in the range of from 185 to 450 millimeters$^3$, with 360 millimeters$^3$ most preferred.

Another important feature of the apparatus 20''' is the substantially cylindrical shape of the subchamber 92'''. This cylindrical shape (together with the frustoconical shape of the deflector 70''') helps maintain the physical integrity of the apparatus 20''' when it is exposed to the above-ambient temperatures and pressures normally experienced during extracorporeal blood treatment. Maintenance of the cylindrical shape of the upper subchamber 92''' is especially important to prevent uneven distortion of upper portions of the wall 52''' (including the deflector 70''') during treatment. Uneven distortion of the upper portions of the upper subchamber 92''' can lead to uneven blood flow in the upper subchamber 92''' during treatment, unexpected volume increases in the upper subchamber 92''' during treatment, and distortion of the deflector 70''' such that blood is not controllably deflected into the upper subchamber 92'''.

Yet another important feature of the apparatus 20''' is the frustoconical shape of the deflector 70'''. As is best shown in the section view of FIG. 14, flatness of the face 96 of the deflector 70''' in the vertical direction presents a flat surface off of which blood is deflected into the upper subchamber 92''', thereby maximizing the controlled mixing of blood in the upper subchamber 92'''.

Another important feature of the apparatus 20''' is the slightly offset position of the upper subchamber 92''' and the opposed offset position of the inlet tube 64''', relative to the lower subchamber 94'''. This offset is created in the blow molding process, in which the upper subchamber 92''' is vertically aligned around a first longitudinal axis and the lower subchamber 94''' is vertically aligned around a second longitudinal axis, which is parallel to and offset from the first longitudinal axis. This relative orientation of the upper and lower subchambers 92''' and 94''' and the inlet tube 64''' creates an asymmetry which eliminates side seams in the lower subchamber 94''' of the apparatus 20''' which might otherwise form during the blow molding process. Side seams are especially detrimental because they can trigger false air alarms by bubble detection equipment. When side seams are eliminated, the blow molded apparatus 20''' is a viable and economical product which lowers the cost of delivery of dialysis services to patients in need.

Other important features of the apparatus 20''' are the level indicator marks 97 and 98. By providing a lower level indicator mark 97, the operator can more easily make sure a predetermined minimum volume of blood is maintained in the upper subchamber 92''' and in the chamber 68'''. A minimum volume of blood in the upper subchamber 92''' is needed to provide blood flowing through the apparatus 20''' an opportunity to be degassed, as previously discussed herein. The upper level indicator mark 98 is used to help the operator maintain a volume of blood in the upper subchamber 92''' which leaves sufficient room for the collection of gases above the upper surface 88''' of the blood.

A still further important feature of the apparatus 20''' are the comparative diameters C (of the chamber across the channel 73), "D" (the diameter of the upper subchamber 92''', and "E" (the diameter of the lower subchamber 94''' above the location at which the wall 52''' tapers inwardly to define the exit port 50'''). In particular, the diameter "D" of the upper subchamber 92''' should neither be substantially larger nor substantially smaller than the diameter "E" of the lower subchamber 94'''. The diameter "E" of the lower subchamber 94''' is typically from 19 to 22 mm, but may be as large as 34 mm, and preferably no less than 80% and no greater than 120% of the diameter "D" of the upper subchamber 92'''. When the diameter "E" is within the preferred range, referred blood flow patterns throughout the apparatus 20''' are more readily achieved.

When the apparatus 20', 20" or 20''' is mounted in a level detector 30 of the extracorporeal treatment system 24 (FIG. 1), proper alignment of the apparatus 20' or 20" within the level detector 30 is achieved, in part, by the narrowing of the housing 32', 32" or 32''' at or below the point where the inlet tube 64", 64' or 64''' turns transversely toward the longitudinal axis of the housing 32' 32" or 32''' respectively In effect, the housing 32' 32" or 32''' functions as a stopper, preventing downward movement of the apparatus 20', 20" or 20''' during operation. By so aligning the apparatus 20', 20" or 20''' within the level detector 30, a proper level of the upper surface 88', 88" or 88''' is more likely to be maintained during extracorporeal treatment.

Each of the bubble trap apparatus 20, 20', 20" and 20''' is preferably constructed of substantially transparent, flexible polyvinyl chloride using conventional blow molding techniques. Clear plastic is selected because it allows the operator to view blood level in the apparatus 20, 20', 20" and 20''' during treatment. Flexibility of the polyvinyl chloride allows the apparatus 20, 20' 20" or 20''' to be adjustably positioned in alignment with the level detector 30. Polyvinyl chloride is typically biocompatible and gamma-sterilizable and thus is suitable for bubble trap apparatus 20, 20', 20" and 20''' through which blood flowing in an extracorporeal treatment system 24 passes.

Presently preferred embodiments of the present invention and many of its improvements have been described with a degree of particularity. It should be understood that the present invention is defined by the spirit and scope of the following claims.

What is claimed is:

1. A method of removing bubbles from blood flowing through a bubble trap apparatus in an extracorporeal blood treatment circuit, said apparatus including a housing having an upper housing end and a lower housing end, the housing defining a substantially vertical chamber extending substantially along a vertical longitudinal axis between said upper and lower housing ends, said chamber having a substantially cylindrical upper subchamber and a lower subchamber, said upper subchamber being offset from said lower subchamber and having upper and lower level indicator marks formed thereon, said method comprising the steps of:

introducing blood into the upper subchamber substantially transversely to the longitudinal axis of the chamber at a position intermediate between the upper and lower housing ends;

deflecting at least a portion of the blood introduced into the chamber with a frustoconical deflector above the position where the blood is introduced into the chamber to form a pool of blood in the chamber in the upper subchamber in a portion of the upper subchamber having a diameter wider than the diameter of the chamber adjacent the frustoconical deflector;

allowing bubbles in the blood to separate from the blood in the pool;

collecting the separated bubbles;

removing the blood from the chamber after the bubbles have been separated therefrom; and maintaining an upper blood surface within the chamber between the upper and lower level indicator marks.

2. An apparatus for trapping bubbles in blood flowing in a circuit, said apparatus comprising:

a housing having an upper housing end and a lower housing end, said housing defining a substantially vertical, cylindrical and elongated interior chamber, said housing having a substantially vertical longitudinal axis;

an inlet tube formed in the housing, having an inlet tube diameter and extending into the chamber substantially transversely to the longitudinal axis of the chamber and at a position intermediate between the upper and lower housing ends, said inlet tube opening into the chamber at a delivery port through which blood is introduced into the chamber, said delivery port having an delivery port diameter;

a substantially frustoconical deflector formed in the housing and having a deflector tip, said deflector projecting into the chamber at a position intermediate between the upper and lower housing ends at the level of the delivery port and defining a narrowed channel of the chamber having a channel diameter narrower than a diameter of the chamber above the deflector and narrower than a diameter of the chamber below the deflector, said deflector positioned to deflect blood introduced through the inlet tube into the chamber above the deflector; and an exit port formed in the housing through which blood is removed from the chamber.

3. The apparatus of claim 2 wherein the blood has an upper blood surface and the apparatus further comprises:

an upper subchamber of the chamber defined at its lower extreme by the channel and its upper extreme by the upper housing end, for mixing the deflected blood and collecting bubbles which have separated from the blood, said upper subchamber having a first longitudinal axis; and a lower subchamber of the chamber defined at its upper extreme by the channel and at its lower extreme by the lower housing end, through which blood flows before removal out the exit port, said lower subchamber having a second longitudinal axis.

4. The apparatus of claim 3 further comprising:

a collar formed in the housing and surrounding the exit port; and a filter having a rim, said filter positioned in the lower subchamber with the filter rim abutting the collar, to filter blood in the lower subchamber before removal of the blood out the exit port.

5. The apparatus of claim 4 further comprising:

a first aperture formed in the housing for removing bubbles from the chamber; and a second aperture formed in the housing for adding fluid and materials to the blood in the chamber.

6. The apparatus of claim 3 further comprising:

an upper blood level indicator mark formed on the housing of the upper subchamber and a lower blood level indicator mark formed on the housing of the upper subchamber at a level intermediate the upper blood level indicator mark and the deflector edge, to provide guidelines between which to maintain the upper blood surface.

7. The apparatus of claim 3 wherein the inlet tube diameter is substantially the same length as the delivery port diameter.

8. The apparatus of claim 3 wherein the channel diameter is greater than the lower subchamber diameter.

9. The apparatus of claim 3 wherein the channel diameter is greater than the diameter of the lower subchamber and the inlet tube diameter is substantially the same length as the delivery port diameter.

10. The apparatus of claim 3 wherein the first longitudinal axis is parallel to and offset from the second longitudinal axis.

11. The apparatus of claim 2 wherein:

the blood flowing in the circuit has a range of flow rates of 50 ml/min to 700 ml/min; and the product of the square of the delivery port diameter multiplied by the channel port diameter is between 185 mm$^3$ and 450 mm$^3$ inclusive.

12. A blow-molded apparatus for trapping bubbles in blood flowing in a circuit, said apparatus comprising:

a housing having an upper housing end and a lower housing end and defining a substantially vertical elongated chamber having a substantially cylindrical upper subchamber and a lower subchamber, said upper subchamber extending along a first longitudinal axis between the upper and lower housing ends and said lower subchamber extending along a second longitudinal axis between the upper and lower housing ends, said first longitudinal axis being parallel to and offset from said second longitudinal axis;

an inlet tube formed integrally with the housing and extending into the upper subchamber of the chamber at a delivery port located at and above a point intermediate between the upper and lower housing ends in a direction substantially transverse to the first longitudinal axis of the upper subchamber for introducing blood into the chamber at a position intermediate between the upper and lower housing ends in a flow direction substantially transverse to the first longitudinal axis, said inlet tube having an inlet tube diameter and said delivery port having a delivery port diameter;

a substantially frustoconical deflector positioned in the chamber adjacent to and spaced apart from the position at which the inlet tube introduces blood into the chamber, the deflector deflecting at least a portion of the blood into the chamber above the deflector, said deflector defining a neck of the housing above which is located the upper subchamber and below which is located the lower subchamber, said chamber having a channel diameter at the level of the neck, wherein said channel diameter is narrower than a diameter of the upper subchamber and narrower than a diameter of said lower subchamber; and an exit port formed in the housing to allow blood to exit the chamber.

13. The apparatus of claim 12 wherein the inlet tube diameter is substantially the same as the delivery port diameter.

14. The apparatus of claim 13 wherein the channel diameter is greater than the diameter of the lower subchamber.

15. The apparatus of claim 14 further comprising:

a collar formed in the housing and surrounding the exit port; and a filter having a rim, said filter positioned in the lower subchamber with the filter rim abutting the collar, to filter blood in the lower subchamber before removal of the blood out the exit port.

16. The apparatus of claim 14 further comprising:

a first aperture formed in the upper end of the housing for removing bubbles from the chamber; and a second aperture formed in the housing at the upper housing end for adding fluid and materials to the blood in the chamber.

17. The apparatus of claim 12 wherein:

the blood flowing in the circuit has a range of flow rates of 50 ml/min to 700 ml/min; and the product of the square of the delivery port diameter multiplied by the channel port diameter is between 185 $mm^3$ and 450 $mm^3$ inclusive.

* * * * *